United States Patent [19]

Rattner

[11] Patent Number: 5,285,772
[45] Date of Patent: Feb. 15, 1994

[54] THERAPY APPARATUS FOR TREATING A PATIENT WITH FOCUSED ACOUSTIC WAVES

[75] Inventor: Manfred Rattner, Grossenseebach, Fed. Rep. of Germany

[73] Assignee: Siemens Aktiengesellschaft, Munich, Fed. Rep. of Germany

[21] Appl. No.: 959,635

[22] Filed: Oct. 13, 1992

[51] Int. Cl.$^5$ .............................................. A61B 17/22
[52] U.S. Cl. ........................... 128/24 EL; 128/660.30; 128/653.1; 378/205
[58] Field of Search ........ 128/24 AA, 24 EC, 660.03, 128/653.1; 378/162, 205

[56] References Cited

U.S. PATENT DOCUMENTS

| | | |
|---|---|---|
| 4,526,168 | 7/1985 | Hassler et al. . |
| 4,697,588 | 10/1987 | Reichenberger . |
| 4,750,487 | 6/1988 | Zanetti ................. 378/162 |
| 4,811,725 | 3/1989 | Grasser ............. 128/240 EL |
| 4,834,074 | 5/1989 | Reichenberger ....... 128/240 EL |
| 4,928,672 | 5/1990 | Grasser et al. . |
| 4,947,830 | 8/1990 | Rattner et al. . |
| 4,984,565 | 1/1991 | Rattner et al. . |
| 5,031,626 | 7/1991 | Hassler et al. .......... 128/660.3 |
| 5,065,761 | 11/1991 | Pell ...................... 128/240 EL |
| 5,070,861 | 12/1991 | Einars et al. ........... 128/240 EL |
| 5,081,984 | 1/1992 | Wess et al. ............. 128/240 EL |
| 5,144,953 | 9/1992 | Wurster et al. .......... 128/240 EL |
| 5,178,135 | 1/1993 | Uchiyama et al. ........ 128/240 EL |

FOREIGN PATENT DOCUMENTS

3426398 3/1986 Fed. Rep. of Germany .
9017444 4/1991 Fed. Rep. of Germany .

*Primary Examiner*—William E. Kamm
*Assistant Examiner*—Brian L. Casler
*Attorney, Agent, or Firm*—Hill, Steadman & Simpson

[57] ABSTRACT

A therapy system for treating a subject with focused acoustic waves for use with a separately available x-ray examination device for forming a high-grade acoustic therapy work station with x-ray locating disclosed. The therapy system includes a therapy head having an x-ray impermeable mark used to align the therapy system with a subject during the x-ray locating, and an acoustic sensing component, which identifies the distance between an acoustic wave source in the therapy head and a region of the subject to be treated, for relatively positioning the subject and the therapy head so that the region is in the focus of the acoustic waves.

23 Claims, 6 Drawing Sheets

THERAPY APPARATUS FOR TREATING A PATIENT WITH FOCUSED ACOUSTIC WAVES

BACKGROUND OF THE INVENTION

1. Field of the Invention

The present invention is directed to a therapy apparatus for treating a patient with focused acoustic waves.

2. Description of the Prior Art

Therapy systems which employ acoustic waves are utilized, for example, for treating stone complaints (lithotripsy), tumors and bone pathologies (osteorestoration). These therapy systems usually are in the form of completely equipped work stations which, in addition to comprising a source of focused acoustic waves with application means for introducing the generated acoustic waves into a patient to be treated, include a locating system and a patient supporting device, whereby the source and the patient supporting device are adjustable relative to one another. During the treatment, the region of the patient to be treated is first localized with the locating system, and the region to be treated is then positioned by adjusting the patient supporting device with the patient thereon and the source relative to one another so that this region is situated in the focus of the acoustic waves. The region to be treated is then charged with acoustic waves in the required way. Although therapy systems having a locating system functioning exclusively on the basis of ultrasound are suitable and are frequently used, therapy systems are normally preferred that have an x-ray locating system, since it is desirable in nearly all applications (and indispensable in many applications) to be able to locate a region to be treated with x-radiation. Some therapy systems have an x-ray locating system, in addition to an ultrasound locating system, since the latter is capable of supplying additional information.

Therapy systems having an x-ray locating system are extremely expensive. This does not represent a disadvantage when the clinic in which the therapy system is operated has an adequately large number of patients in order to enable an economical operation of the therapy system. In the interests of the patient, however, it would be desirable to be able to have a high-performance therapy system of the type described above in smaller clinics or in a doctors's office as well. In the case of a therapy system equipped with an x-ray locating device, however, the comparatively high price thereof does not allow an economical utilization of the therapy system under those conditions.

SUMMARY OF THE INVENTION

An object of the present invention is to offer a simple and economic therapy system that allows a high-grade work station with x-ray locating to be installed in small clinics and potentially even in doctors' offices.

This object is achieved in accordance with the principles of the present invention in a therapy system for treating a patient with focused acoustic waves having a source of focused acoustic waves with which the focused acoustic waves can be introduced into an acoustic propagation medium, these waves converging in a focus lying on the acoustic axis of the source, the source having an x-ray-transparent region through which the acoustic axis of the source proceeds; application means for introducing the focused acoustic waves generated with the source into a patient to be treated; an x-ray impermeable mark arranged on the acoustic axis; and acoustic means for identifying the distance of a region to be treated with focused acoustic waves from the source.

The invention is based on the assumption that an x-ray device having a patient support table, adjustable at least in a plane intersecting the central ray of the x-ray emission at a right angle, but preferably fully spatially adjustable is present in all smaller clinics and even often in doctors' offices, or at least a simple x-ray device, for example a C-arm device, and a spatially adjustable patient bearing table, for example an operating table or urological table, are available. When the therapy device of the invention and the x-ray device are aligned relative to one another such that the central ray of the x-ray device coincides with the acoustic axis of the source, this creates the conditions for adjusting the position of the patient on the support table under x-ray supervision, so that the acoustic axis of the source proceeds through a region to be treated. To that end, the patient must merely be displaced relative to the source with the patient support table so that the image of the x-ray impermeable mark coincides in the x-ray image with the image of the region to be treated. Thereupon, the patient and the focus of the acoustic waves must be shifted relative to one another in the direction of the acoustic axis, using the means for identifying the distance of the region to be treated from the source, so that the distance of the region to be treated from the source of acoustic waves is equal to the distance of the focus of the acoustic waves from the source of acoustic waves. The region to be treated is then located in the focus of the acoustic waves, whereupon the treatment with acoustic waves can ensue in the required way.

A high-grade work station for treating a patient with focused acoustic waves, which offers x-ray locating, can be realized with the therapy system of the invention and equipment which is already present. This equipment, i.e. an x-ray device with an adjustable patient support table or a C-arm device and a patient support table, can continue to be employed for their conventional purposes as needed, since no permanent connection whatsoever is produced to the therapy system of the invention. The distance identifying means can be a pressure sensor, an ultrasound applicator, or some other type of acoustic device. Even if an ultrasound applicator is not used as the distance identifying means, an ultrasound applicator can still be introduced into the x-ray-transparent region, so that there is the possibility of obtaining additional information about the region to be treated.

Although European Application 0 372 119 discloses a therapy system for treating a patient with focused acoustic waves that includes a source of focused acoustic waves having an x-ray transparent region, and application means for introducing the focused acoustic waves into the patient to be treated, the locating of a region to be treated ensues herein with an x-ray locating system that forms a component part of the therapy means. The x-ray radiation proceeds through the x-ray transparent region of the source. The locating of a region to be treated ensures in such a way that the x-ray locating system is pivoted around an axis in order to transirradiate the patient to be treated from two different directions. On the basis of the x-ray images obtained in this way, the region to be treated is aligned such that it lies at the intersection of the central rays belonging to the two transirradiation directions. Subsequently, the source is set such that the focus of the acoustic waves is located in the intersection. Moreover, an ultrasound locating system is provided that can be introduced into the x-ray-transparent region. There is no suggestion, however, that the x-ray locating system and the ultrasound locating system be applied in combination in such a way for locating a region to be treated that only the distance of the region to be treated from the source is identified with the ultrasound locating system, and the locating otherwise ensues exclusively using the x-ray locating means.

German Gebrauchsmuster 90 17 441 discloses an aiming device for a lithotriptor, wherein the locating of a calculus to be disintegrated ensues exclusively with an x-ray locating system that transirradiates the patient to be treated from different angles. The aiming device has a plurality of x-ray impermeable marks that allow the x-ray locating means (which is a conventional C-arm x-ray system separate from the lithotriptor) and the lithotriptor to be aligned relative to one another in the required way. The x-ray impermeable marks also allow the patient to be adjusted relative to the lithotriptor so that the calculus to be treated is located in the focus of the lithotriptor. Acoustic means for identifying the distance of the calculus to be disintegrated are not provided. On the contrary, the locating ensures exclusively on an x-ray basis.

As noted above, the means for identifying the distance of the region to be treated from the source can be a diagnostic ultrasound applicator according to one version of the invention, this being introducible into the x-ray transparent region of the source. Such an ultrasound applicator can be used exclusively for distance measuring (i.e., not for imaging purposes) or for imaging, or both. The focus of the acoustic waves and the body of the patient can be easily shifted relative to one another in the direction of the acoustic axis of the source on the basis of the marking on the picture screen of the ultrasound display device, connected to the ultrasound applicator, which indicates the position of the focus of the acoustic waves in the ultrasound image. The patient and the focus are shifted relative to one another such that the image of the region to be treated coincides with the marking in the ultrasound image visible on the picture screen. The ultrasound applicator is preferably a B-scan applicator that, when introduced into the x-ray-transparent region, assumes such a position that the plane of the body of the patient scanned with the ultrasound applicator contains the acoustic axis of the source. It is especially advantageous that the ultrasound applicator and the associated ultrasound display device can be employed for other purposes independently of the therapy system of the invention.

In a preferred embodiment of the invention, the means for identifying the distance of a region to be treated from the pressure pulse source include a pressure sensor, means for the pulsed operation of the source and means for measuring a time span of acoustic wave travel, corresponding to the distance of the region to be treated from the source. This time span ends with the appearance of an output signal of the pressure sensor that corresponds to the echo arising by reflection from the region to be treated of the acoustic wave that arose on the basis of the pulsed actuation of the source. Given the arrangement of the pressure sensor in the propagation path of the acoustic waves, for example, a time span can be measured for this purpose that elapses between two pulsed output signals of the pressure sensor that appear following the pulsed actuation of the source. The two pulse-like output signals of the pressure sensor are respectively caused by a signal arising upon passage of the generated acoustic wave through the pressure sensor on its way from the source to the region, and by the weaker signal that arises when the parts of the generated acoustic wave reflected at the region to be treated pass through the pressure sensor. The time elapsing between the pulse-like output signals of the pressure sensor thus represent a measure for the distance of the region to be treated from the pressure sensor. Since the distance of the pressure sensor from the source or from the focus of the acoustic waves is known, shifting the patient to be treated and the focus of the acoustic waves relative to one another in the direction of the acoustic axis of the source makes it easily possible to assure that the time between the two pulse-like output signals of the pressure sensor is equal to the transit time that a pressure pulse requires for covering the distance (in more exact terms, for covering twice the distance) of the pressure sensor from the focus of the acoustic waves. When these times coincide, this means that the region to be treated lies in the focus of the acoustic waves, as desired. Since this adjustment procedure can make it necessary to repeatedly actuate the source in pulsed fashion, it can be expedient in the interests of patient comfort to actuate the source for pulsed operation so that it generates acoustic waves of diminished intensity. Since it is not only the distance of the pressure sensor from the focus of the acoustic waves but also the distance of the focus from the source that are known, it is also possible to measure the pulse-like output signal arising upon passage of the parts of the generated acoustic wave reflected at the region to be treated through the pressure sensor. In this case, it is adequate that the pressure sensor be arranged in the propagation path of the reflected parts of the acoustic waves. It can then be assured by shifting the patient to be treated and the focus of the acoustic waves relative to one another in the direction of the acoustic axis of the source that the time between the pulse-like actuation of the source and the output signal of the pressure sensor to be taken into consideration is equal to the transit time that a pressure pulse requires for covering the sum of the distance of the source from the focus of the acoustic waves and the distance of the focus of the acoustic waves from the pressure sensor.

As has already been mentioned, the region to be treated is introduced into the focus of the acoustic waves by shifting the patient and the focus of the acoustic waves relative to one another in the direction of the acoustic axis of the source. This, for example, can occur by moving the patient support table in this direction. According to an advantageous embodiment of the invention, however, the source is provided with means for displacing the focus of the acoustic waves along the acoustic axis of the source. This displacement means, for example, can be fashioned such that the source is adjustable in the direction of its acoustic axis relative to the applicator housing as disclosed in European Appliccation 0 328 943, corresponding to U.S. Pat. No. 4,947,830. It is especially advantageous, however, when the means for displacing the focus of the acoustic wave contain an acoustic lens with variable focal length according to one version of the invention. It thus becomes possible to achieve a relatively large displacement range of the focus along the acoustic axis of the source in a space-saving way.

Preferably a control means is provided that automatically sets the means for displacing the focus of the acoustic waves on the basis of the output signals of the means for identifying the distance of the region to be treated from the source, such that the distance of the region to be treated from the source is equal to the distance of the focus of the acoustic waves from the source. When, thus, the patient has been aligned relative to the therapy system so that the image of the region to be treated coincides with the image of the x-ray impermeable mark, the focus of the acoustic waves is automatically displaced with reference to the output signals of the pressure sensor such that the focus is located in the region to be treated. Treatment with acoustic waves then follows.

In order to facilitate the alignment of the x-ray device and the therapy system relative to one another, a second x-ray impermeable mark can be arranged at the distance of the x-ray impermeable mark on the acoustic axis in a further version of the invention. The correct alignment of the therapy system and the x-ray device relative to one another can then be simply recognized from the fact that the two marks coincide.

In order to preclude disturbing influences of the acoustic propagation medium on the image quality of the x-ray images serving the purpose of x-ray locating, an x-ray transparent tube can be provided in an embodiment of the invention that displaces the acoustic propagation medium from the x-ray transparent region at least during passage of the x-ray radiation through the x-ray transparent region of the source. At least one x-ray-impermeable mark is applied to the x-ray transparent tube. In an especially advantageous embodiment of the invention, at least the source and the applicator are combined to form a therapy head that is attached to a carriage displaceable on the floor. A compact structure of the therapy device is thus achieved. The carriage can also contain the units required for the operation of the therapy system.

In order to enable above-table as well as under-table applications of the therapy system, a further embodiment of the invention the therapy head is attached to the carriage pivotable by 180° around an essentially horizontal axis. It is self-evident that the patient support table must have an adequately large opening or interruption for the application of the applicator to the body of the patient to be treated in the case of under-table application.

DESCRIPTION OF THE PREFERRED EMBODIMENTS

Figure 1:
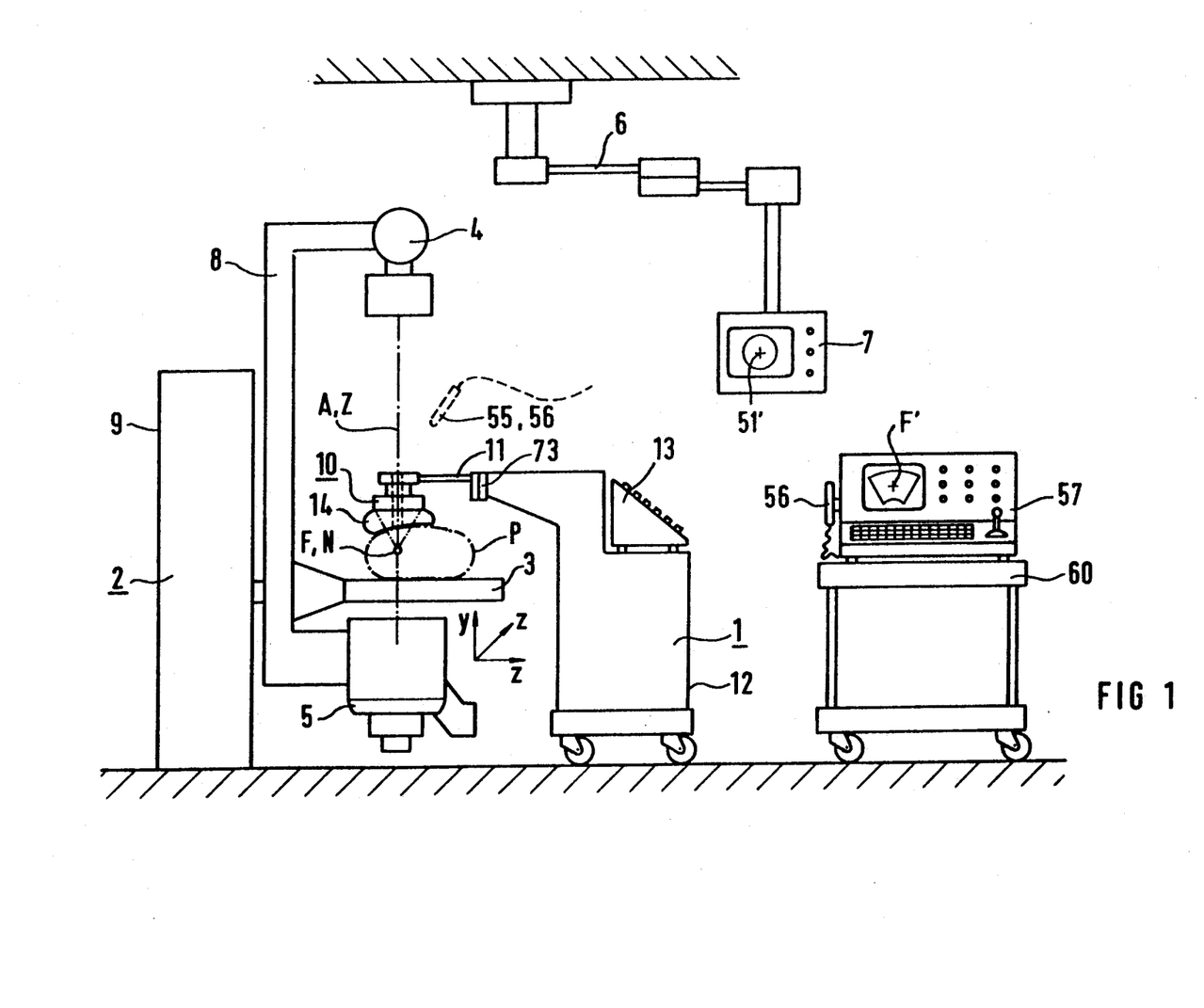
FIG. 1 is a side elevational view of a therapy system constructed in accordance with the principles of the present invention, interacting with an x-ray examination device, in a schematic representation.

FIG. 1 shows the therapy device of the invention generally referenced 1, interacting with an x-ray examination system, generally referenced 2. The latter includes a patient support table 3, an x-ray radiator 4 arranged thereabove and an x-ray image intensifier 5 arranged under the patient support table 3. The image of the output luminescent screen of the x-ray image intensifier 5 is picked up with a video camera in a known way and is displayed at a monitor 7, mounted in adjustable fashion at the ceiling of the examination room with a bracket 6. The x-ray radiator 4 and the x-ray image intensifier 5 are secured to a carrier 8 lying opposite one another, this carrier 8 being aligned such that the central ray Z of the x-ray beam emanating from the x-ray radiator 4 proceeds vertically. The carrier 8 and the patient support table 3 are attached to a stand 9. The patient support table 3 is adjustable in the direction of the three spatial axes x, y, z, preferably by motor drive. At least the movements in the x and z directions, i.e. in the direction of the longitudinal axis of the patient support table 3 and transversely relative thereto, ensue independently of the carrier 8 and, thus, of the x-ray radiator 4 and the x-ray image intensifier 5. By adjusting the patient support table 3 in these two directions, the central ray Z of the x-ray beam can be made to proceed through different body regions of a patient lying on the patient support table 3. An x-ray device of the described type is distributed, for example, by Siemens under the name "UROSKOP B2".

The therapy device 1 has a therapy head, generally referenced 10, that is secured via a holder 11 to a carriage 12 that can be moved on the floor of the treatment room. The carriage 12 contains all units required for the operation of the therapy head 10. A control panel 13 that has a keyboard and a monitor (see FIG. 3) that are required for operating the therapy device, which contains the control electronics for the therapy device 1, is also on the carriage 12. The therapy head 10 contains a central, x-ray-transparent region (indicted with broken lines in FIG. 1) and is aligned relative to the x-ray examination system 1 (as described below) such that the central ray Z thereof proceeds through the x-ray-transparent region. The therapy head 10 presses against the body surface of the patient P with an x-ray-transparent application cushion 14 so as to introduce the focused acoustic waves generated with the therapy device 1 into the body of the patient P.

Figure 2:
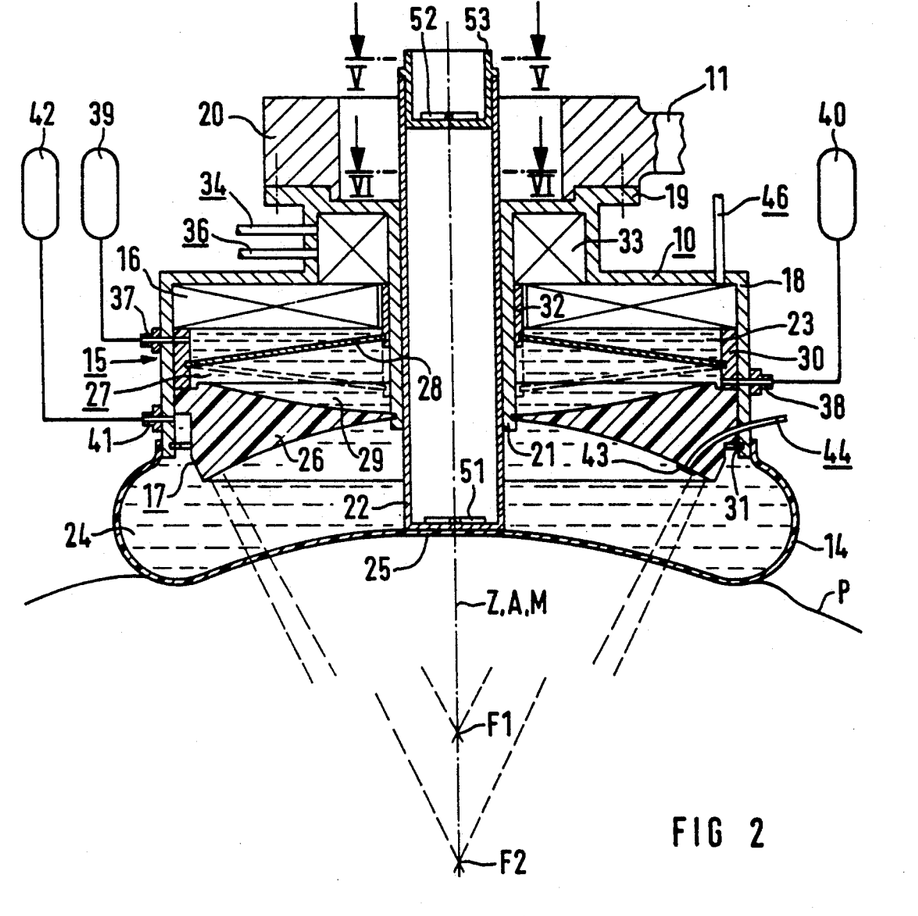
FIG. 2 is a schematic illustration of a longitudinal section through the therapy head of the therapy system of FIG. 1.

As may be seen from FIG. 2, the therapy head 10 contains a pressure pulse generator, generally referenced 15, as the source of focused acoustic waves. This pressure pulse generator 15 includes an electromagnetic pressure pulse source 16 (not shown in detail) and an acoustic positive lens, generally referenced 17. The positive lens 17 focuses the pressure pulses emanating from the pressure pulse source 16 onto a focus F, which is a three-dimensional focal zone in practice. The focus F lies on the acoustic axis A of the pressure pulse generator 15 that corresponds to the middle axis M (FIG. 2) of the pressure pulse generator 15. The pressure pulse generator 15 is fashioned approximately rotationally-symmetrically relative to the axis M. The pressure pulse source 16 and the lens 17 are accepted in a housing 18, having an end remote from the pressure pulse source 16 closed liquid-tight with an elastic-flexible application cushion 14. The pressure pulse source 16, for example, is an electromagnetic pressure pulse source as disclosed in European Application 0 188 750, corresponding to U.S. Pat. No. 4,697,588 and European Application 0 301 360, corresponding to U.S. Pat. No. 4,928,672 in terms of structure and function. At its other end neighboring the pressure pulse source 16, the housing 18 has a mounting flange 19 that serves the purpose of securing the therapy head 10 to a mounting ring 20 of the carrier 11 by screws, only the center lines of two screws being indicated with broken lines in FIG. 2. A tube 22 having a closed lower end is introduced into the bore of the inside wall 21, this tube 22 being formed of an x-ray-transparent material, for example Plexiglass ®. The tube 22 is accepted in the bore of the inside wall 21 in axially displaceable fashion and liquid-tight. Sealants, not shown in FIG. 2, can be provided. The space situated between the pressure pulse source 16 and the positive lens 17 as well as the space situated between the positive lens 17 and the application cushion 14 are respectively filled with water 23 and 24 as an acoustic propagation medium.

The region of the therapy head 10 situated within the inside wall 21 represents an x-ray-transparent region from which the water 24 can be displaced with the tube 22 in order to avoid negative influences on the image quality. When the therapy head 10 is applied to the body surface of the patient P indicated in FIG. 2, the tube 22 is thereby introduced into the bore of the inside wall 21 to such an extent that its base 25 presses against the body surface of the patient P with the application cushion 14 therebetween.

The positive lens 17 is composed of a solid lens 26 and a liquid lens generally referenced 27. The solid lens 26 is biconcavely shaped and is formed of a material, for example polystyrol, wherein the acoustic propagation speed is higher in the water 24 provided as the acoustic propagation medium. The solid lens 26 consequently acts as positive lens. The inner edge of the annular solid lens 26 is introduced liquid-tight into a channel in the outer surface of the inside wall 21. The solid lens 26 has an outer circumference introduced liquid-tight into the housing 18. The liquid lens 27 has a lens fluid 29 enclosed between an entry wall 28 and that side of the solid lens 26 facing toward the pressure pulse source 16. The outer edge of the entry wall 28 formed, for example, of polymethylpentene (TPX) or of polytetrafluor-ethylene (PTFE) is accepted liquid-tight in a circumferential channel of a retaining ring 30. The retaining ring 30 is accepted in axially non-displaceable fashion between the pressure pulse source 16 and the solid lens 26, whereby the solid lens 26 is held axially non-dislocatable with a snap ring 31. The outer surface of the retaining ring 30 presses liquid-tight against the housing 18. The inner circumferential edge of the entry wall 28 is accepted in a circumferential channel of a sleeve 32 surrounding the inside wall 21 in liquid-tight fashion. The sleeve 32 is longitudinally displaceable on the inside wall 21 with a schematically indicated adjustment mechanism 33, which can be an electric motor with suitable gearing. The adjustment mechanism 33 is in communication with a drive unit 35 (see FIG. 3) via a line generally referenced 34. The focal length of the liquid lens 27 and, thus, the overall focal length of the positive lens 17 can be varied by displacing the sleeve 32 between an ultimate position shown with solid lens in FIG. 2 and another ultimate position indicted with broken lines in FIG. 2.

When, as in the case of the illustrated exemplary embodiment, the lens fluid 29 is a liquid wherein the acoustic propagation speed is lower than in the water 23 provided as acoustic propagation medium (for example, Flutec ® EP 3 or Fluorinert ® FC 75), the liquid lens 27 functions as a positive lens at the ultimate position shown with solid lens in FIG. 2. As the sleeve 32 is gradually displaced in the direction toward its other ultimate position, the focused effect of the liquid lens 27 diminishes and gradually changes into a slightly defocusing effect. The liquid lens 27 thus acts as a dispersion lens in its ultimate position indicated with broken lines. The effect on the position of the focus of the pressure pulses generated with the pressure pulse source 16 and focused with the positive lens 17 is that the focus F1 situated closer to the pressure pulse source 16 is obtained at the ultimate position shown with solid lines in FIG. 2 and the focus F2 at a greater distance therefrom is obtained at the ultimate position indicated with broken lines. The focus F of the pressure pulses can be displaced with continuous variation between these two ultimate positions dependent on the position of the sleeve 32 along the acoustic axis A of the pressure pulse generator 15. The adjustment mechanism 33 contains a position generator (not shown), for example an inductively acting position generator, that generates a signal corresponding to the position of the sleeve 32, and thus to the position of the focus F that has been set, via a line generally referenced 36.

Since, when adjusting the sleeve 32, the volumes respectively situated between the pressure pulse source 16 and the entry wall 28 and, between the entry wall 28 and the solid lens 26 change, respective connecting branches 37 and 38 (schematically shown) are provided. The branches 37 and 38 respectively connect the aforementioned volumes to schematically indicated compensation vessels 39 and 40 that contain water or lens fluid. This permits a volume compensation to ensue in the required way both with respect to the water 23 as well as with respect to the lens fluid 29. Such a volume compensation can also ensue with respect to the water 24 when the volume situated between the solid lens 26 and the application cushion 14 changes upon introduction of the tube 22, when the application cushion 14 is pressed against the patient P, since a further connecting branch 41 with an associated compensating vessel 42 are also provided.

A pressure sensor 43 is attached to that side of the solid lens 26 facing away from the pressure pulse source 16. The pressure sensor 43, for example, is a sensor formed of a piezoelectrically activated polymer foil that is distributed by Pennwalt, Great Britain, under the name "Kynar ®-Piezo-Film SDT 1-028k". The pressure sensor 43 is in communication with an evaluation circuit 45 (FIG. 3) via a line generally referenced 44. The pressure pulse source 16 connected, via a schematically indicated high-voltage cable 46, to a high-voltage pulse generator 47 (FIG. 3) situated in the carriage 12. When the pressure pulse 16 is charged with a high-voltage pulse from the pulse generator 47 for outputting a pressure pulse, the pressure sensor 43 generates two successive, pulse-like signals. The first of these signals arises as the pressure pulse emanating from the pressure pulse source 16 passes through the pressure sensor 43 on its path to the focus and the second, weaker of these signals arises as the parts of the pressure pulse reflected at the region to be treated, for example a calculus, a bone or a tumor, inside the body of the patient P pass through the pressure sensor 43.

Figure 3:
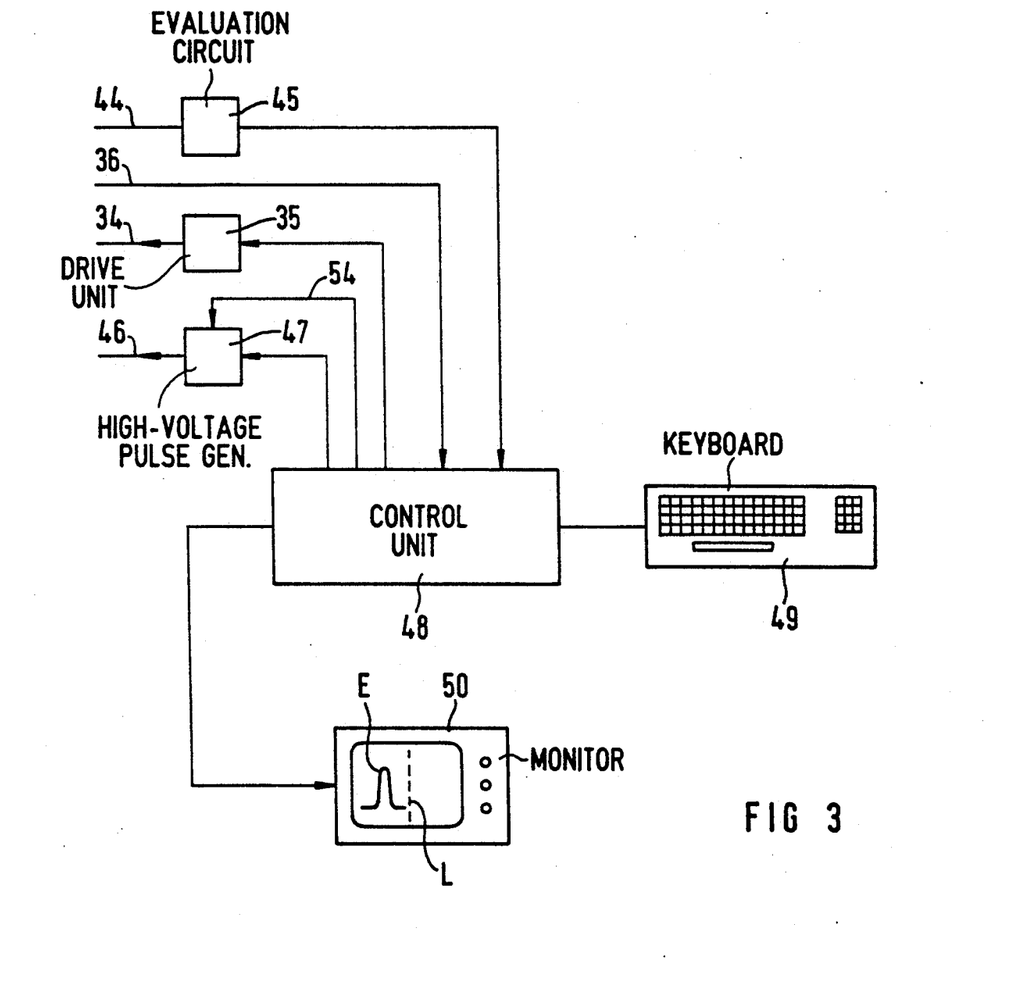
FIG. 3 is a block circuit diagram of the therapy system according to FIGS. 1 and 2.
Figure 4:
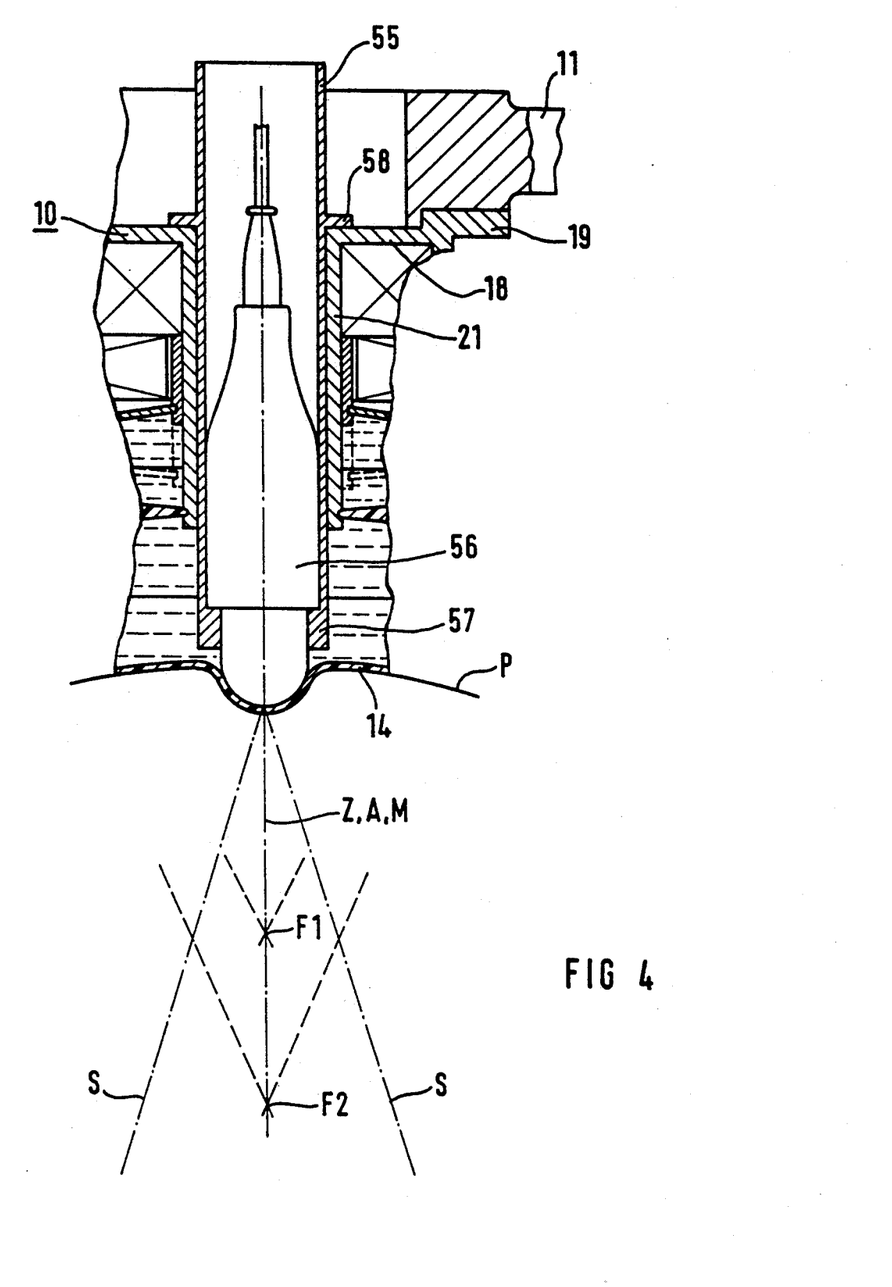
FIG. 4 is a schematic illustration of a partial, longitudinal section through the therapy head according to FIG. 2, in another operating condition.

The block circuit diagram of the therapy device 1 is shown in FIG. 3. An electronic control unit 48 is provided for controlling the functions of the therapy device 1, a keyboard 49 that serves the purpose of operating the therapy device 1 being connected to this electronic control unit 48. The drive unit 35 is connected to the control unit 48, this drive unit 35 serving the purpose of adjusting the focal length of the liquid lens 27 via the line 34. The line 36 is also connected to the control unit 48, with which the signal corresponding to the focal length of the positive lens 17 is supplied to the control unit 48. Further, the high-voltage pulse generator 47 is connected to the control unit 48, which charges the pressure pulse source 16 with a high-voltage pulse via the high-voltage cable 46 when it is actuated by the control unit 48. In addition, the evaluation circuit 45 is connected to the control unit 48, from which the control unit 48 receives a signal corresponding to the distance of the region to be treated from the pressure sensor 43. Finally, a monitor 50 is connected to the control unit 48. A vertical line L whose horizontal position on the picture screen corresponds to the distance of the focus F from the pressure pulse 16 is mixed in the image on the monitor 50. The position of the line L is changed by the control unit 48 on the basis of the signal of the position generator supplied to it via the line 36 dependent on the distance of the focus F from the pressure pulse source 16 that has been set. The echoes E of the pressure pulses received with the pressure sensor 43 are also mixed into the image of the monitor 50 in the form of a spike pulse, whereby the region to be treated is situated closer to the pressure pulse source 16 the farther left of the line L the echo E is displayed. The region to be treated is situated farther from the pressure pulse source 16 the farther the echo E is displayed to the right of the line L. The region to be treated is situated in the focus F of the pressure pulse source 16 when the line L proceeds centrally through the echo E.

Figure 5:
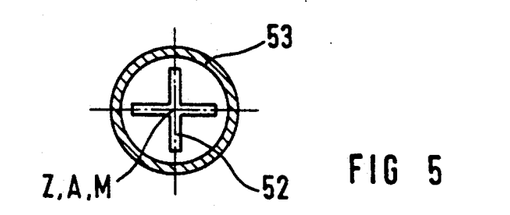
FIGS. 5 and 6 respectively show a part of the therapy head according to FIG. 2 in a section along the lines V—V and VI—VI in FIG. 2.
Figure 6:
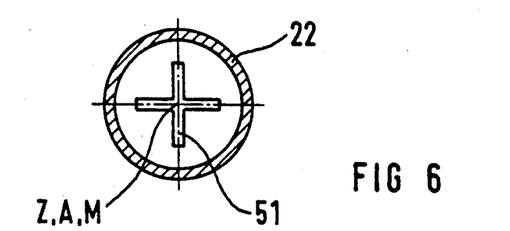

In order to be able to align the therapy device 1 and the x-ray examination device 2 relative to one another in the way required for the implementation of a treatment such that the central ray Z of the x-ray examination device 2 coincides with the acoustic axis A of the therapy device 1, an x-ray impermeable mark is applied on the base 25 of the tube 22, this mark lying on the acoustic axis A. In the described exemplary embodiment, this is a lead cross 51 (also see FIG. 6) whose two legs intersect in a point lying on the acoustic axis A. A second x-ray-impermeable mark is also provided, also lying on the acoustic axis A and being arranged at a distance from the other mark, i.e. the lead cross 51. In the described exemplary embodiment, the second mark is a second lead cross 52 (also see FIG. 5) that is applied to the floor of an auxiliary tube 53 introducible into the tube 22. The legs of the lead cross 52 also intersect in a point that lies on the acoustic axis A.

In order to align the therapy device 1 and the x-ray examination device 2 relative to one another in the desired way, these devices merely need to be brought into such a position relative to one another under x-ray supervision that the intersections of the legs of the two lead crosses 51 and 52 coincide in the x-ray picture shown on the monitor 7. The base 25 of the tube 22 lies against the inside of the application cushion 14. When the crosses 51 and 52 coincide, the central ray Z and the acoustic axis A coincide, these proceeding vertically, i.e. in the direction of the y-axis, in the case of the exemplary embodiment of FIGS. 1 through 7. When this is the case, the therapy device 1 and the x-ray examination device 2 are locked in place such that dislocations of the acoustic axis A and of the central ray Z relative to one another will not occur. The auxiliary tube 53 can now be removed.

For treating a patient, for example a patient P having a kidney stone N, the patient support table 3 is first brought into its lowest position. The patient P is then placed on the patient support table 3 on his stomach, in such a position that the kidney having the kidney stone N is located in the region of the central ray Z and the acoustic axis A. The x-ray examination device 2 is then activated. The patient is now positioned by adjusting the patient support table 3 in the direction of the x and z axes so that the image 51' of the lead cross 51 coincides with the image of the kidney stone N (not shown) on the monitor 7. So that the patient P is not unnecessarily exposed to x-radiation, the x-ray examination device 2 is now initially deactivated. The patient support table 3 is then adjusted upwardly in the direction of the acoustic axis A and the central ray Z, i.e. in the direction of the x-axis, until the application cushion 14 of the therapy head 10 presses flush against the body surface of the patient P. By exerting metered pressure on the tube 22, it is assured that it presses against the body surface of the patient P with the application cushion 14 therebetween. When this is the case, the x-ray examination device 2 is re-activated and another check is undertaken with reference to the x-ray image visible on the monitor 7 to determine whether the image 51' of the lead cross 51 still coincides with the kidney stone N. If dislocations happen to have occurred due to the described application procedure, these are corrected by adjusting the patient support table 3 in the direction of the x and z axes. The x-ray examination device 2 is then deactivated again. The high-voltage pulse generator 47 can be switched from a therapy mode to a locating mode by the control unit 48 via a control line 54 by appropriate actuation of the keyboard 49. In the locating mode the pulse generator 47 emits pressure pulses having highly diminished intensity. The pulse generator 47 is now switched to this locating mode by appropriate actuation of the keyboard 49. With reference to the echoes E of the reduced-energy pressure pulses shown on the monitor 50 and reflected at the kidney stone N, and with reference to the line L, the focal length of the liquid lens 27 is now set by appropriate actuation of the keyboard 49 so that the line L proceeds centrally through the echo E in the image on the monitor 50. Since the kidney stone N is now not only situated on the acoustic axis A but also is situated in the focus F of the pressure pulses, the treatment can begin. To this end, the high-voltage pulse generator 47 is switched to the therapy mode by appropriate actuation of the keyboard 49. Previously, the tube 22 was retracted from the propagation path of the pressure pulses, if necessary.

During the therapy mode, the kidney stone N is charged with a plurality of pressure pulses, preselectable with the keyboard 49. These intensify on their propagation path through the water 23, the lens fluid 29, the water 24 and the body tissue of the patient P to form shock waves, which are pressure pulses having an extremely steep leading front. Under the action of the shock waves, the kidney stone N disintegrates into small fragments that can be eliminated in a natural way. At any time during and at the end of the therapy mode, there is the possibility, by inserting the tube 22 and activating the x-ray examination device 2, to check whether the kidney stone N is still located on the acoustic axis A and the central ray Z. Moreover, there is also the possibility at any time to switch from the therapy to the locating mode in order to check whether the kidney stone N is still situated in the focus F.

After the end of the therapy, the patient support table 3 is again lowered into its lowest position and the patient P is removed.

Important, additional information can be acquired when the tube 22 is withdrawn from the therapy head 10 and a tube 55 is instead inserted into the bore of the inside wall 21, the tube 55 containing the ultrasound head 56 of a conventional diagnostic ultrasound device 57. The ultrasound device 57 is placed on a carriage 60 in the proximity of the therapy device 1. The ultrasound head 56 is preferably a B-scan applicator that is accepted in the tube 55 such that it scans a slice that contains the acoustic axis A of the pressure pulse source 16, and thus the focus F of the pressure pulses. The limits of the scannable slice are entered with broken lines and referenced S in FIG. 4. The bore of the tube 55 is provided with a shoulder 57 against which the housing of the ultrasound head 56 presses, so that a defined position of the ultrasound head 56 in the tube 55 is guaranteed. The ultrasound head 56 is accepted in the bore of the tube 55 in liquid-tight and axially non-disclocatable fashion in a manner within the knowledge of a person having ordinary skill in the art. The tube 55 can be manually turned around the acoustic axis A, so that arbitrary slices containing the acoustic axis A can be scanned with the ultrasound head 56. In order to assure that the application of the ultrasound head 56 presses flush against the body surface of the patient P, with the application cushion 14 therebetween in the way required for good image quality, the tube 55 is provided with a flange 58 that presses against the housing 18 when the ultrasound head 56 is correctly applied.

The ultrasound head 56 and the ultrasound device 57 are particularly useful in those instances wherein adequate information about a region to be treated are not obtained with the ultrasound examination device 2. The ultrasound head 56 and the ultrasound device 57, however, can also be employed in order to position a region to be treated, that is already aligned so as to lie on the acoustic axis A, such that it lies in the focus F of the pressure pulses. To this end, a mark F' is applied, for example glued, to the picture screen of the ultrasound device 57, this mark F' indicating the position of the focus of the pressure pulses in the ultrasound image for a defined position of the entry wall 28, for example the ultimate position thereof for which the focus F2 at a greater distance is obtained. It is self-evident that the position of the marking F' is valid for the position of the ultrasound head 56 shown in FIG. 4. The region to be treated can then be easily positioned such that it is located in the focus of the pressure pulses, by adjusting the patient support table 3 in the y-direction such that the image (not shown in FIG. 1) of the region N to be treated coincides with the mark F' in the ultrasound image.

Figure 7:
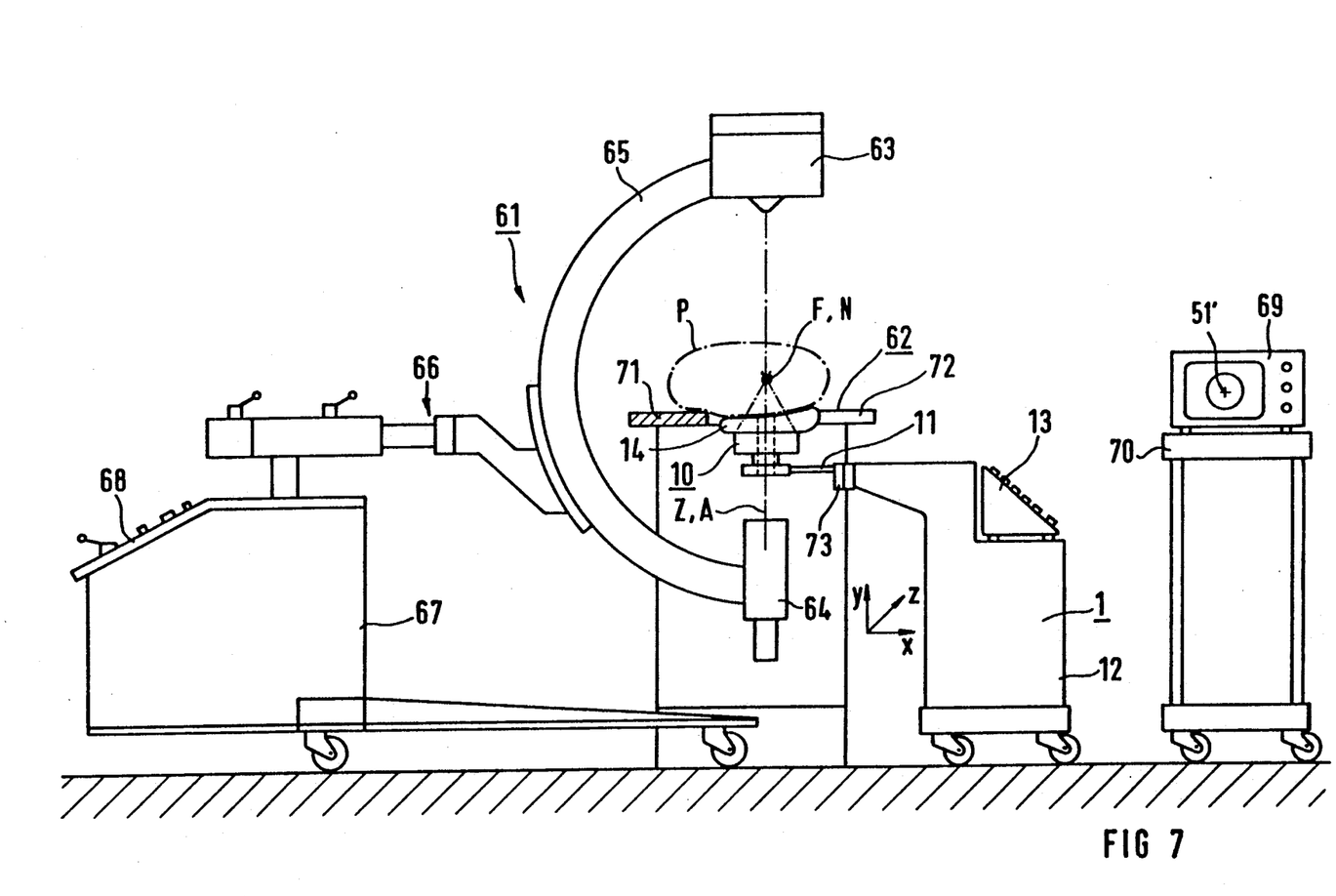
FIG. 7 is a side elevational view of a therapy device of the invention in collaboration with a C-bend x-ray device and an operating table.

The work station according to FIG. 7 differs from that set forth above in that the x-ray examination device 2 is replaced by a known C-arm x-ray device 61 as distributed, for example, by Siemens AG under the name "SIREMOBIL 3" and an operating table 62 is provided. The portable C-arm x-ray device 61 has an x-ray radiator 63 and an x-ray image intensifier 64 that are attached to the ends of the C-arm 65 lying opposite one another. The C-arm 65 is adjustably connected to the carriage 67 via a holder 66 in a known way. A control panel 68 for the C-arm x-ray device 61 is provided at the carriage 67 that contains the units required for the operation of the x-ray radiator 63 and the x-ray image intensifier 64. The monitor 69 for this control panel 68 is placed in the proximity of the therapy device 1 on a movable carriage 70.

The operating table 62 preferably has a motor-driven patient support plate 71 adjustable in the direction of the three spatial axes x, y, z, which is provided with a cutout 72. The latter serves the purpose of being able to apply the therapy head 10—which is in an under-the-table position—to a patient P lying on his back on the operating table 62. In order to be able to also utilize the therapy head 10 in an over-the-table position, the holder 11 is connected to the carriage 12 via an articulation 73 that allows the therapy head 10 to be pivoted by 180° vis-a-vis the position shown in FIG. 1, so that the acoustic axis A also proceeds vertically in the case of FIG. 7. The required alignment of a C-arm x-ray device 61 and of the therapy device 1 relative to one another such that the central ray Z of the C-arm x-ray device 61 coincides with the acoustic axis A of the therapy head 10 again ensues with reference to the lead crosses 51 and 52. As a result of the versatile possibilities of adjusting the C-arm x-ray device 61, the required alignment is facilitated. When the correct alignment has been found, both the therapy device 1 and the C-arm x-ray device 61 are locked in their respective positions.

The treatment procedure ensues as set forth above.

An important advantage of the therapy system of the invention is that it forms a high-grade work station with x-ray locating by interaction with components already present, for example the x-ray examination device 2 and, potentially, the ultrasound device 57 or the C-arm x-ray device 61 and the operating table 62, whereby the components required in addition to the therapy device 1 can be returned to other uses at any time. A renewed combination of these components with the therapy device 1 presents no special problems. The therapy system of the invention thus also enables smaller clinics and even doctors' offices to have a high-grade therapy system for treating patients with focused acoustic waves available in an economic way.

In both exemplary embodiments, the therapy head 10 has an acoustic lens with a variable focal length. The displacement of the patient and the focus F of the pressure pulses relative to one another along the acoustic axis A therefore preferably ensues by varying the focal length of the positive lens 17. Only when this possibility of adjustment is inadequate is the patient adjusted relative to the therapy head 10 in the direction of the acoustic axis A with the patient support table 3, or the operating table 62, in order to bring the region to be treated into the focus F of the pressure pulses. It is also possible within the framework of the invention, however, to use a therapy head that has an acoustic positive lens with fixed focal length. In this case, the relative positioning of the region to be treated and the focus F of the pressure pulses in the direction of the acoustic axis ensues exclusively by adjusting the patient support table 3, or the operating table 62, in the direction of the acoustic axis, or of the y-axis. In the case of a therapy head having a positive lens with a fixed focal length, the ultrasound device 57 with the ultrasound head 56 can also be employed for locating purposes when a mark whose position corresponds to the position of the focus of the acoustic waves, is glued on the picture screen of the ultrasound device 57.

The control unit 48 can be fashioned such that it initiates the emission of a pressure pulse with reduced intensity during the therapy mode before every pressure pulse of high intensity, or after defined plurality of pressure pulses with high intensity. In this way, dislocations of the patient P relative to the therapy head 10 can be recognized on the monitor 50 during the therapy mode without requiring a manual switching from therapy to locating mode and vice versa.

When it is assured—for example, by catch positions or the like at the x-ray examination device 2, or at the C-arm x-ray device 61 and at the therapy device 1, that both the central ray Z and the acoustic axis A proceed in the same, defined direction, for example vertically, both lead crosses 51 and 52 are not absolutely necessary for aligning the devices relative to one another. One of the two then suffices.

After the alignment of the therapy device 1 with the x-ray examination device 2, or with the C-arm x-ray device 61, has been accomplished, there is also the possibility of replacing the tube 22 having the lead cross 51 by a tube without x-ray-impermeable marking, when the location at which the lead cross 51 was imaged is previously provided with a suitable marking, for example a sticker, on the picture screen of the monitor 7, or 69.

A pressure pulse generator having an electromagnetic pressure pulse source is provided in the above-described exemplary embodiments. The therapy device of the invention, however, can also contain some other types of pressure pulse generator that, for example, a piezoelectric pressure pulse source. A separate element such as an acoustic lens, need not be used to focus the acoustic wave source itself can be suitably shaped for focusing the waves. Different generators of acoustic waves can be used, for example an ultrasound generator, instead of a pressure pulse generator. Particularly in this case, there is the possibility of utilizing the therapy device for hyperthermic treatment methods. It is also clear that therapy devices constructed in accordance with the principles of the present invention can be utilized not only for lithotripsy, as set forth in conjunction with the exemplary embodiments, but also for other medical purposes.

Although modifications and changes may be suggested by those skilled in the art, it is the intention of the inventor to embody within the patent warranted hereon all changes and modifications as reasonably and properly come within the scope of his contribution to the art.

I claim as my invention:

1. A therapy system for treating a region of a subject with focused acoustic waves comprising:
   a source of acoustic waves having an acoustic axis along which said acoustic waves propagate;
   means for focusing said acoustic waves to a focus on said acoustic axis;
   applicator means, containing an acoustic propagation medium, adapted to be disposed between said source and a region of said subject to be treated, for coupling said acoustic wave into said subject;
   an x-ray impermeable mark disposed on said acoustic axis; and
   means for acoustically identifying a distance between said source and a region of said subject to be treated for use in relatively positioning said source and said subject.

2. A therapy system as claimed in claim 1 wherein said applicator means has a central opening extending therethrough along said acoustic axis forming an x-ray transparent region, and said system further comprising an ultrasound applicator optionally disposable in said x-ray transparent region.

3. A therapy system as claimed in claim 1 wherein said applicator means has a central opening extending therethrough along said acoustic axis forming an x-ray transparent region, and wherein said means for acoustically identifying a distance comprises a diagnostic ultrasound applicator disposed in said x-ray transparent region when identifying a distance.

4. A therapy system as claimed in claim 1 wherein said means for identifying a distance comprises:
   pressure sensor means, adapted to be disposed in a propagation path of said acoustic waves between said source and said region of said subject, for generating an electrical signal when traversed by an acoustic wave;
   means for pulsed operation of said source of acoustic waves; and
   means connected to said pressure sensor means for measuring a time span corresponding to the distance between said source and said region of said subject, said time span ending with the generation of a signal by said pressure sensor means corresponding to an echo from said region of said subject resulting from the pulse-like operation of said source.

5. A therapy system as claimed in claim 4 wherein said means for pulsed operation of said source is a means for causing said source to generate acoustic waves with an intensity reduced in comparison to an intensity of acoustic waves used for therapy.

6. A therapy system as claimed in claim 1 wherein said source includes means for displacing said focus along said acoustic axis.

7. A therapy system as claimed in claim 6 wherein said means for displacing said focus comprises an acoustic lens with a variable focal length.

8. A therapy system as claimed in claim 6 further comprising:
   control means for automatically displacing said focus along said acoustic axis, on the basis of signals from said means for identifying a distance, so that the distance of said region to be treated from said source is equal to the distance of the focus from said source.

9. A therapy system as claimed in claim 1 further comprising:
   a further x-ray impermeable mark disposed on said acoustic axis spaced from said x-ray impermeable mark.

10. A therapy system as claimed in claim 1 wherein at least said applicator means has an x-ray transparent region, and said therapy system further comprising:
    an x-ray transparent tube disposed in said applicator means along an acoustic axis, said tube displacing said acoustic propagation medium out of said x-ray transparent region.

11. A therapy system as claimed in claim 10 wherein said x-ray impermeable mark is disposed on said tube.

12. A therapy system as claimed in claim 1 wherein said source and said applicator means form, in combination, a therapy head, and further comprising a carriage supporting said therapy head and means for moving said carriage on a floor of an examination room.

13. A therapy system as claimed in claim 12 wherein said therapy system includes a plurality of components including said therapy head, and wherein said components are mounted on said carriage.

14. A therapy system as claimed in claim 12 further comprising means for pivoting said therapy head through 180° around a substantially horizontal axis.

15. A therapy system as claimed in claim 1 wherein at least said source has an x-ray transparent region through which said acoustic axis extends.

16. A therapy system as claimed in claim 15 wherein said x-ray transparent region comprises a substantially centrally disposed opening in said source.

17. A therapy system as claimed in claim 15 wherein said system further comprises a diagnostic ultrasound applicator optionally disposable in said x-ray transparent region.

18. A therapy system as claimed in claim 15 wherein said means for acoustically identifying a distance comprises a diagnostic ultrasound applicator disposed in said x-ray transparent region when identifying a distance.

19. A therapy system as claimed in claim 15 further comprising:
an x-ray transparent tube extending through said x-ray transparent region for displacing said acoustic propagation medium out of said x-ray transparent region.

20. A therapy system as claimed in claim 19 wherein said x-ray impermeable mark is disposed on said tube.

21. A therapy system for treating a region of a subject with focused acoustic waves comprising:
a source of acoustic waves having an acoustic axis along which said acoustic waves propagate;
means for focusing said acoustic waves to a focus on said acoustic axis;
applicator means, containing an acoustic propagation medium, adapted to be disposed between said source and a region of said subject to be treated, for coupling said acoustic waves into said subject;
an x-ray impermeable mark disposed on said acoustic axis; and
means for exclusively acoustically identifying a distance between said source and a region of said subject to be treated for use in relatively positioning said source and said subject.

22. A therapy system as claimed in claim 21 wherein said means for exclusively acoustically identifying a distance comprises:
pressure sensor means, adapted to be disposed in a propagation path of said acoustic waves between said source and said region of said subject, for generating an electrical signal when traversed by an acoustic wave;
means for pulsed operation of said source of acoustic waves; and
means connected to said pressure sensor means for measuring a time span corresponding to the distance between said source and said region of said subject, said time span ending with the generation of a signal by said pressure sensor means corresponding to an echo from said region of said subject resulting from the pulse-like operation of said source.

23. A therapy system as claimed in claim 21 wherein at least said applicator means has an x-ray transparent region, and wherein said means for exclusively identifying a distance comprises:
an ultrasound applicator disposed in said x-ray transparent region; and
non-imaging means for operating said ultrasound applicator solely for identifying said distance.

* * * * *

UNITED STATES PATENT AND TRADEMARK OFFICE
CERTIFICATE OF CORRECTION

PATENT NO. : 5,285,772
DATED : February 15, 1994
INVENTOR(S) : Manfred Rattner

It is certified that error appears in the above-indentified patent and that said Letters Patent is hereby corrected as shown below:

On the cover page, immediately below the filing date, insert:

--[30] Foreign Application Priority Data
October 24, 1991 [DE] Fed. Rep. of Germany...4135177--.

Signed and Sealed this

First Day of November, 1994

Attest:

BRUCE LEHMAN

Attesting Officer

Commissioner of Patents and Trademarks